(12) United States Patent
Tsuchihashi et al.

(10) Patent No.: US 7,036,390 B2
(45) Date of Patent: May 2, 2006

(54) METHOD FOR DETECTING HUMAN BODY IN A VEHICLE

(75) Inventors: Choichiro Tsuchihashi, Kobe (JP); Yasushi Shinojima, Kobe (JP)

(73) Assignee: Fujitsu Ten Limited, Kobe (JP)

( * ) Notice: Subject to any disclaimer, the term of this patent is extended or adjusted under 35 U.S.C. 154(b) by 0 days.

(21) Appl. No.: 10/399,808

(22) PCT Filed: Aug. 8, 2002

(86) PCT No.: PCT/JP02/08141

§ 371 (c)(1),
(2), (4) Date: Apr. 23, 2003

(87) PCT Pub. No.: WO03/019236

PCT Pub. Date: Mar. 6, 2003

(65) Prior Publication Data

US 2004/0020314 A1    Feb. 5, 2004

(30) Foreign Application Priority Data

Aug. 24, 2001   (JP) .............................. 2001-254528

(51) Int. Cl.
*G01N 19/00*   (2006.01)

(52) U.S. Cl. ................................... 73/865.9

(58) Field of Classification Search ............ 73/865.9; 340/545.3, 552, 584, 589, 448; 701/47
See application file for complete search history.

(56) References Cited

U.S. PATENT DOCUMENTS

| | | | | |
|---|---|---|---|---|
| 4,914,422 A | * | 4/1990 | Rosenfield et al. | ...... 340/573.1 |
| 5,329,949 A | * | 7/1994 | Moncourtois et al. | .... 134/57 R |
| 5,510,765 A | * | 4/1996 | Madau | ...................... 340/541 |
| 5,790,032 A | | 8/1998 | Schmidt | |
| 6,028,509 A | | 2/2000 | Rice | |
| 6,220,627 B1 | * | 4/2001 | Stanley | ...................... 280/735 |
| 6,252,240 B1 | * | 6/2001 | Gillis et al. | ............ 250/559.38 |
| 6,639,512 B1 | * | 10/2003 | Lee et al. | ................ 340/425.5 |
| 2001/0038698 A1 | * | 11/2001 | Breed et al. | .................. 381/86 |
| 2002/0080014 A1 | * | 6/2002 | McCarthy et al. | .......... 340/426 |
| 2003/0038722 A1 | * | 2/2003 | Khairallah et al. | ......... 340/584 |

FOREIGN PATENT DOCUMENTS

DE   43 35 773 A1   4/1995

(Continued)

OTHER PUBLICATIONS

Patent Abstract of Japan, Publication No. 08113106 A, Published on May 07, 1996, in the name of Nakazawa, et al.

(Continued)

*Primary Examiner*—Charles Garber
(74) *Attorney, Agent, or Firm*—Christie, Parker and Hale, LLP

(57) ABSTRACT

A synthetic wave is obtained which represents the synthesis of a transmitted wave radiated from a sensor and a reflected wave returned from a breathing human body, and the presence or absence of a human in the vehicle is detected from the envelope of the synthetic wave. When the presence of a human is detected continuously for a predetermined length of time, it is determined that a human is present in the vehicle.

11 Claims, 14 Drawing Sheets

FOREIGN PATENT DOCUMENTS

| | | |
|---|---|---|
| EP | 0 742 449 A2 | 11/1996 |
| EP | 0 792 778 A2 | 9/1997 |
| GB | 2 322 029 A | 8/1998 |
| JP | 8-113106 A | 5/1996 |
| JP | 08113106 A * | 5/1996 |
| JP | 8-507706 | 8/1996 |
| JP | 9-507647 | 8/1997 |
| JP | 9-228679 A | 9/1997 |
| JP | 9-236671 | 9/1997 |
| JP | 9-254633 | 9/1997 |
| JP | 9-254633 A | 9/1997 |
| JP | 09228679 A * | 9/1997 |
| JP | 09254633 A * | 9/1997 |
| JP | 2001-160192 A | 6/2001 |
| JP | 2001160192 A * | 6/2001 |
| WO | WO 93/23833 | 11/1993 |
| WO | WO 94/20021 | 9/1994 |
| WO | WO 95/11458 | 4/1995 |
| WO | WO 95/20170 | 7/1995 |

OTHER PUBLICATIONS

Patent Abstract of Japan, Publication No. 09228679 A, Published on Sep. 02, 1997, in the name of Ueda.

Patent Abstract of Japan, Publication No. 09236671 A, Published on Sep. 09, 1997, in the name of Schimko, et al.

Patent Abstract of Japan, Publication No. 09254633 A, Published on Sep. 30, 1997, in the name of Kasai.

Patent Abstract of Japan, Publication No. 2001160192 A, Published on Jun. 12, 2001, in the name of Terada, et al.

International Search Report, dated Sep. 16, 2004, for Application No. 02755883.2-1264, for applicant Fujitsu Ten Limited.

Page from Webster's Encyclopedic Unabridged Dictionary of the English Language, definition of the term "Envelope".

International Search Report of corresponding international Application No. PCT/JP02/08141, dated Sep. 17, 2002.

* cited by examiner

IN PHASE ($\theta=0°$)

OUT OF PHASE ($\theta=90°$)

WHEN PHASES ARE OPPOSITE TO EACH OTHER ($\theta=180°$), AMPLITUDE OF SUM WAVE BECOMES SMALL.

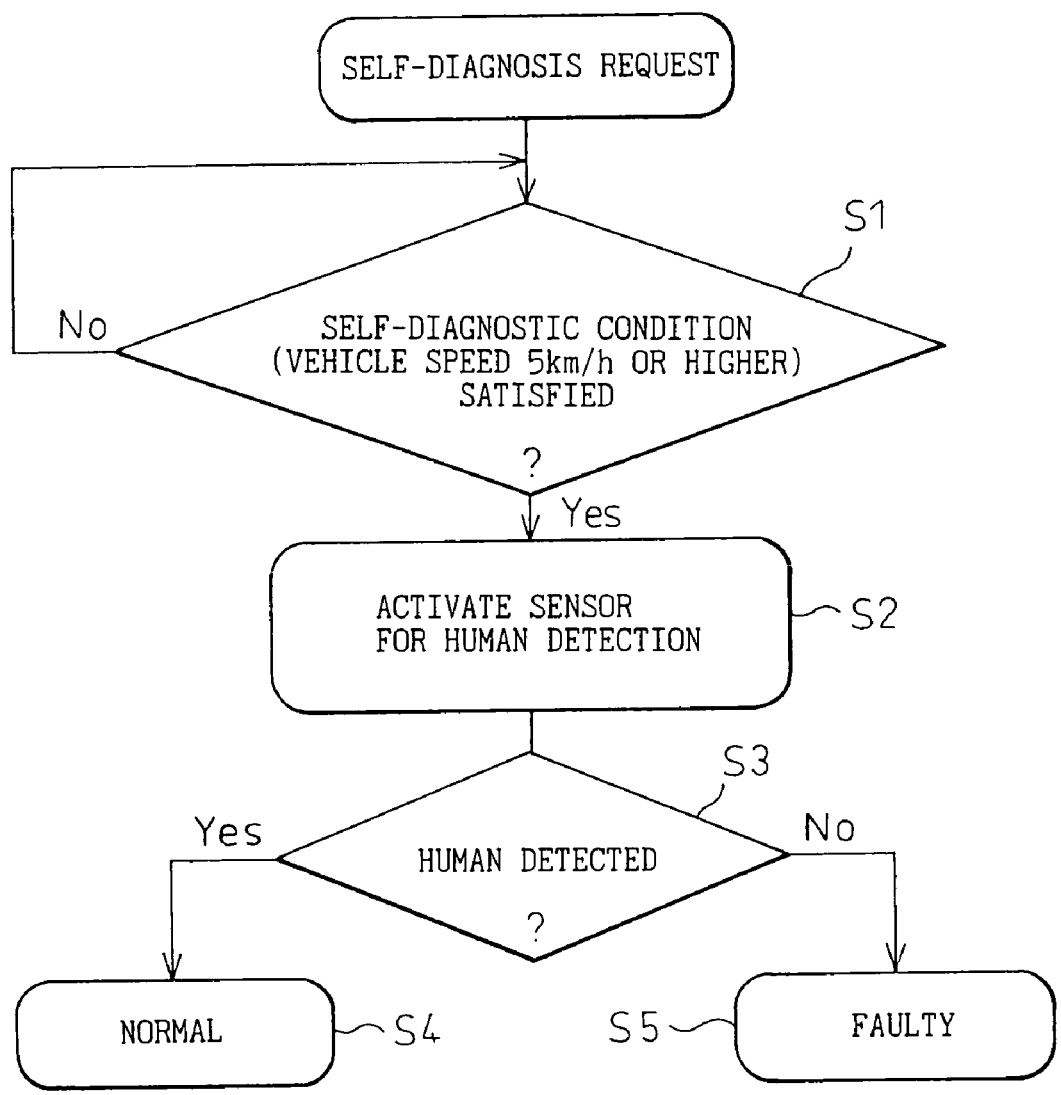

METHOD FOR DETECTING HUMAN BODY IN A VEHICLE

CROSS-REFERENCE TO RELATED APPLICATION

This application is a National Phase Patent Application of International Application Number PCT/JP02/08141, filed on Aug. 8, 2002, which claims priority of Japanese Patent Application Number 2001-254528, filed Aug. 24, 2001.

TECHNICAL FIELD

The present invention relates to a method for detecting the presence of a human body and, more particularly, to a method for detecting the presence of a human body in a vehicle.

BACKGROUND ART

There often occur such accidents as a child being left in a vehicle under the intense heat of summer and dying, because of heat, in the vehicle. To prevent the occurrence of such a tragedy, a system is being studied that detects the presence of a human inside a vehicle, and that issues some kind of alarm when the temperature inside the vehicle becomes excessively high.

FIG. 1 shows one example of a sensor designed to detect the presence of a human, such as an intruder in a vehicle. In the figure, reference numeral 1 is the sensor, and 2 is an object, in this case, a human body such as an intruder. In the sensor 1, an oscillator 11 produces an output, for example, of 2.45 GHz, and this output is radiated from a transmitting antenna 12 toward the human body 2. The reflected wave from the human body 2 is received by a receiving antenna 13, and mixed in a frequency converter 14 with a portion of the transmitted wave to produce a beat signal.

When a moving object is detected inside the vehicle, the sensor determines it as being an intruder. The detection of a moving object is done utilizing the Doppler effect. For example, a radio wave of 2.45 GHz is radiated from the transmitting antenna 12 toward the object 2, and the radiated radio wave is reflected by the human body 2 and received by the receiving antenna 13. If the human body is moving, the reflected wave is slightly shifted in frequency due to the Doppler effect. When the transmitted frequency is fo, for example, the reflected frequency is fo+Δ. Here, the amount of shift, Δ, is derived from the following equation.

$$\Delta = \text{Reflected frequency} - \text{Transmitted frequency} = (2v/c)fo \quad (1)$$

v: Relative velocity of human body 2 with respect to sensor c: Velocity of light As can be seen from the above equation, the value of Δ is extremely small compared with the frequency of the transmitted wave fo. For example, when the transmitted frequency is 2.45 GHz, Δ is on the order of several tens of Hz. Since it is difficult to measure the amount of shift Δ directly, beats occurring between the transmitted wave and the received wave are measured, and a signal of a frequency equal to the amount of shift Δ is output.

However, if the presence of a child quietly sleeping in a vehicle is to be detected, the only movement that can be detected is the slight movement of the chest associated with the breathing action of the child. In the case of an infant, the chest movement generated by breathing is about 2 mm in amplitude and 0.2 to 0.5 Hz in frequency. If the frequency is 0.5 Hz, for example, the speed of the chest movement is no more than 2 mm per second. Such a minuscule and slow-speed movement is difficult to detect by utilizing the Doppler effect. For example, when the transmitted frequency is 2.45 GHz, the Doppler frequency (the amount of shift Δ) produced by the movement of 2 mm per second is 0.03 Hz according to the above equation. That is, it takes $\frac{1}{0.03}$ seconds to obtain a waveform of one cycle. However, since the breathing motion is about 0.5 Hz in frequency, the direction of the motion is reversed before the waveform can be obtained. Therefore, in such a region, the Doppler effect does not occur (Problem 1).

Conventionally, a microwave is used as the transmitted wave, but microwaves have the property that they are reflected by electrically conductive objects but pass through nonconductive objects. As a human body is electrically conductive and therefore reflects microwaves, the advantage is that the chest movement can be observed without being affected by clothes, etc. However, the microwave sensor has the shortcoming that it is susceptible to external disturbances because, as shown in FIG. 2, the transmitted wave passes through the vehicle's windshield which is electrically nonconductive. In FIG. 2, the sensor 1 detects the presence of the human 2 inside the vehicle R, but it also detects through the windshield G the movement of a human P outside the vehicle. On the other hand, as the movement to be detected in the vehicle is a very small breathing motion, the sensor sensitivity must be increased but, in that case, the sensor becomes more sensitive to movements outside the vehicle (Problem 2).

Accordingly, it is an object of the present invention to provide a method for detecting a human body in a vehicle, that can detect a very small movement associated, for example, with the breathing motion of a sleeping child.

DISCLOSURE OF THE INVENTION

To solve the above-described problems, according to the method of the present invention, a synthetic wave is obtained which represents the synthesis of a transmitted wave radiated from a sensor and a reflected wave returned from a breathing human body, and the presence or absence of a human in the vehicle is detected from the envelope of the synthetic wave. The frequency of the transmitted wave is 4.7 GHz or higher.

When the presence of a human is detected continuously for a predetermined length of time, it is determined that a human is present in the vehicle.

When the interior of the vehicle reaches a temperature dangerous to a human, the sensor is activated.

A device for monitoring temperature gradient inside the vehicle is provided, and the sensor is activated in advance when it is predicted by the device that the interior of the vehicle is likely to reach a dangerous temperature.

When the rate of change of temperature inside the vehicle is mild, the sensor is operated at random timing for a predetermined length of time.

When the interior of the vehicle reaches a dangerous temperature, and when the presence of a human is detected, an alarm is issued. The dangerous temperature is a temperature high enough or low enough to present a hazard to a human body.

When the presence of a human has not been detected throughout the duration of a predetermined time, the sensor is deactivated.

The sensor is operated in a situation where a person is undoubtedly present in the vehicle, and if the presence of the person is detected, it is determined that the sensor is operating normally, but if the presence of the person is not detected, it is determined that the sensor is faulty.

According to the present invention, a synthetic wave is obtained which represents the synthesis of the transmitted wave radiated from the sensor and the reflected wave returned from a breathing human body, and the presence or absence of a human in the vehicle is detected from the envelope of the synthetic wave. Especially, by setting the frequency of the transmitted wave at 4.7 GHz or higher, it becomes possible to detect a slight movement associated with a breathing motion, and thus the presence of a child quietly sleeping in a vehicle can be detected.

Further, since provisions are made to activate the sensor when the temperature inside the vehicle has reached or is expected to reach a level dangerous to a human, the chance of detecting a movement of a person outside the vehicle is reduced. Furthermore, when the rate of change of temperature is mild, the sensor is operated for a predetermined length of time at random timing, and this serves to save energy.

BRIEF DESCRIPTION OF THE DRAWINGS

FIG. 19 is a diagram showing a flowchart for a still further embodiment of the present invention.

DETAILED DESCRIPTION OF THE INVENTION

Figure 3:
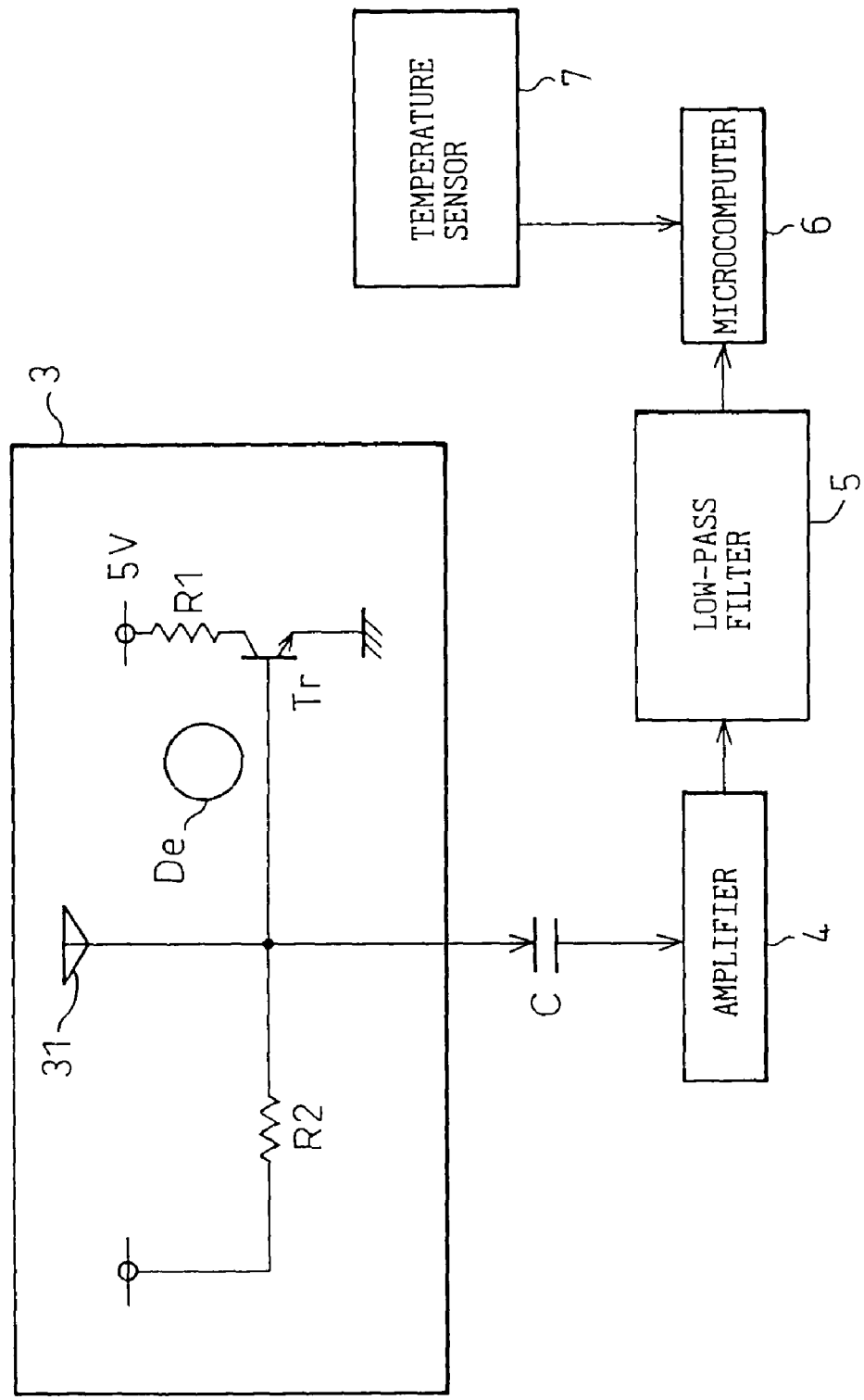
FIG. 3 is a diagram schematically showing the configuration of a sensor using a dielectric resonator according to a method of the present invention.

FIG. 3 is a diagram schematically showing the configuration of a sensor 3 using a dielectric resonator according to a method of the present invention. In FIG. 3, De is the dielectric resonator, and Tr is a transistor whose collector is connected to a power supply via a resistor R1, and whose emitter is grounded. The base of Tr is connected to the power supply via a resistor R2, and also connected to an amplifier 4 via a capacitor C as a differentiator. A radio wave emitted from the dielectric resonator De is radiated from a transmit-receive antenna 31 toward an object, and the reflected wave is received via the transmit-receive antenna 31. A synthetic wave signal, representing the synthesis of the waveform of the transmitted wave from the dielectric resonator and the waveform of the reflected wave from the object, is applied to the base of the transistor Tr. Then, the base voltage, i.e., the synthetic wave signal, is differentiated by the capacitor C and supplied to the amplifier 4 for amplification. The amplified output is fed to a microcomputer 6 via a low-pass filter 5. Reference numeral 7 is a temperature sensor, and the microcomputer 6 is adjusted in accordance with temperature changes.

Figure 4:
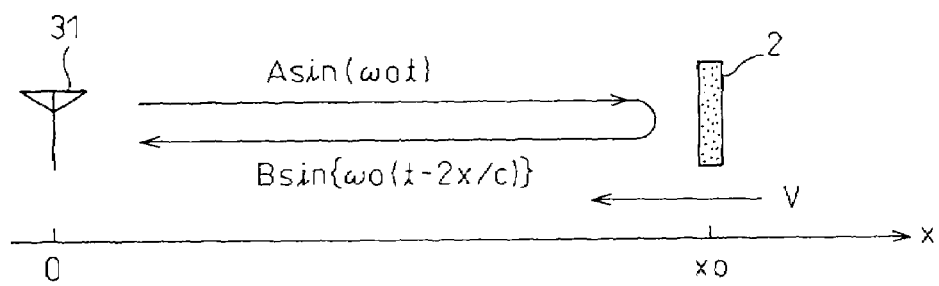
FIG. 4 is a diagram showing the principle of operation of the method of the present invention for detecting a minuscule movement by using a microwave.

FIG. 4 is a diagram showing the principle of operation of the method of the present invention for detecting a minuscule movement by using a microwave. In FIG. 4, $x_0$ indicates the position of an object at t=0; when the transmitted wave $A\sin(\omega_0 t)$ radiated from the transmit-receive antenna 31 is reflected by the object 2 approaching at a velocity v, the reflected wave is given as $B\sin\{\omega_0(t-2x/c)\}$. Here, x is the position of the object 2, and c is the velocity of light. If $x = x_0 - vt$, then the reflected wave is given as $$B \sin [\omega_0\{t-2(x_0/c-vt/c)\}]$$

$$B \sin [\omega_0(1+2v/c)t - \omega_0(2x_0/c)] \quad (2)$$

The Doppler effect is observed when v in the first term $\omega_0(1+2v/c)t$ of equation (2) is constant for a sufficient length of time. However, in the case of a minuscule movement such as a body movement produced by breathing, since the object is exhibiting an up/down movement constantly changing the direction of the movement between the positive and negative directions, v itself can be regarded as a function of the time t. On the other hand, the following assumption is also possible. That is, since v is sufficiently small, the object can be considered stationary by assuming that v=0.

Figure 5:
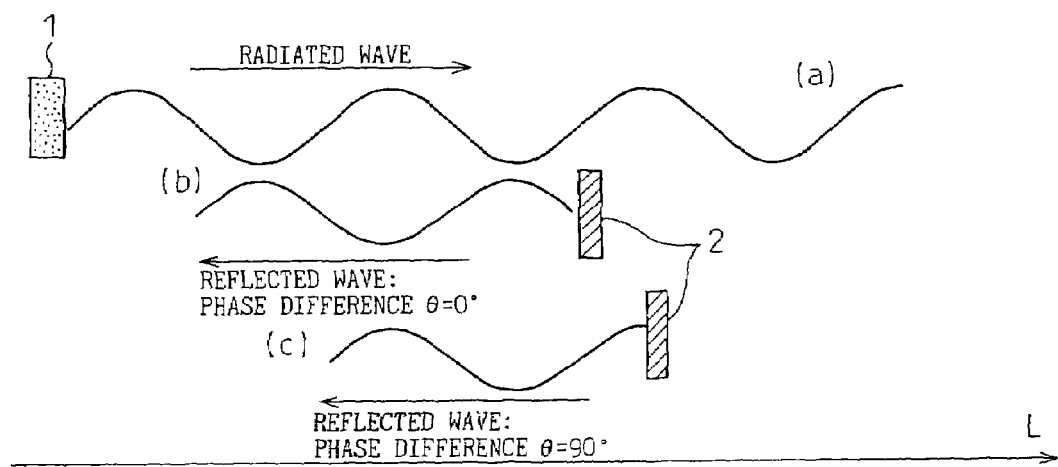
FIG. 5 is a diagram showing the phase relationship between a wave radiated from a sensor and a wave reflected from an object.

FIG. 5 is a diagram showing the phase relationship between the wave radiated from the sensor 1 and the wave reflected from the object 2. As shown in FIG. 5, the phase difference of the wave reflected from the stationary object is a function of the distance L between the object and the sensor. In FIG. 5, (a) shows the waveform of the radiated wave, (b) the waveform of the reflected wave with a phase difference of 0, and (c) the waveform of the reflected wave with a phase difference of 90°. The phase difference between the reflected wave and the radiated wave is determined by the distance between the sensor 1 and the human body 2.

Figure 6A:
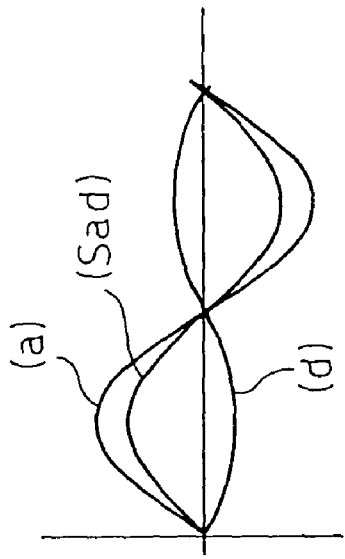
FIGS. 6A to 6C are diagrams each showing the relationship between the radiated wave, the reflected wave, and their synthetic wave.
Figure 6B:
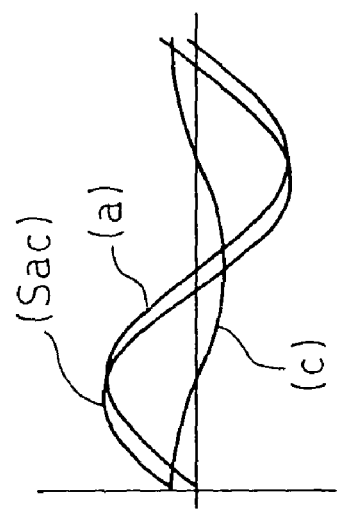
Figure 6C:
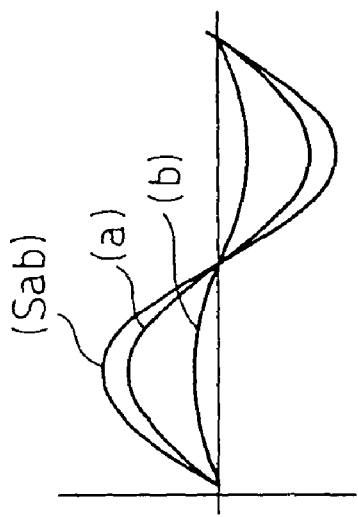

FIGS. 6A to 6C are diagrams each showing the relationship between the radiated wave (a) and the reflected wave and their synthetic wave. FIG. 6A shows the synthetic wave (Sab) when the phase difference θ of the reflected wave (b) is 0. FIG. 6B shows the synthetic wave (Sac) when the phase difference θ of the reflected wave (c) is 90°. FIG. 6C shows the synthetic wave (Sad) when the phase difference θ of the reflected wave (d) is 180°.

Figure 7:
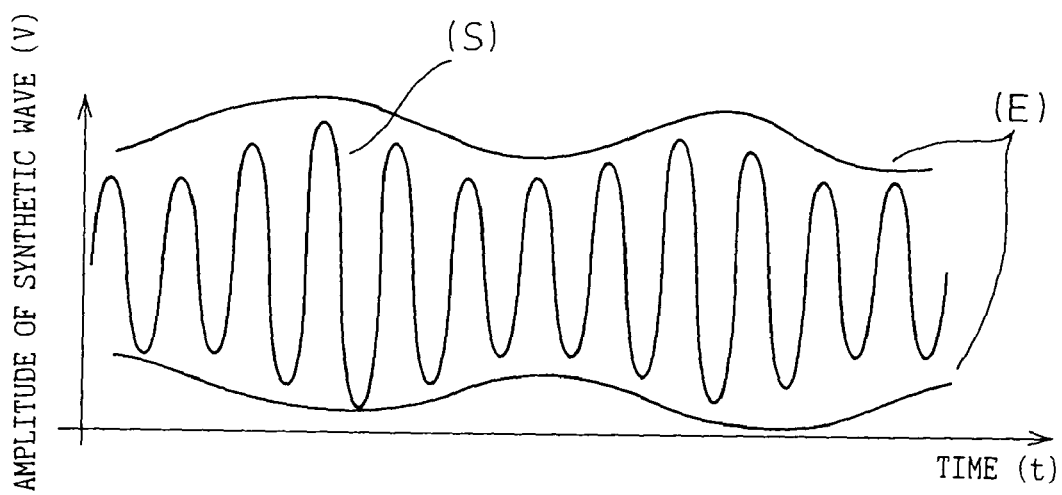
FIG. 7 is a diagram showing the envelope of the synthetic wave when the object is moving.

As can be seen from FIGS. 6A to 6C, the waveform of the synthetic wave produced by combining the radiated wave, i.e., the transmitted wave, with the received wave varies with the distance between the object and the sensor, provided that the size of the object and the material of its surface remain the same. Therefore, when the object is moving, the synthetic wave (S) varies as shown in FIG. 7. When the envelope (E) of the synthetic wave (S) is differentiated and the amount of change of the envelope is extracted, a signal proportional to the relative velocity of the object can be obtained.

However, the movement to be detected from a human at rest in a vehicle is the up/down movement of the chest or abdomen associated with the breathing action of the human, and the frequency of this movement is 0.2 to 0.3 Hz and its amplitude is only 1 to 2 mm. The resulting motion waveform is shown in FIG. 8.

Figure 8:
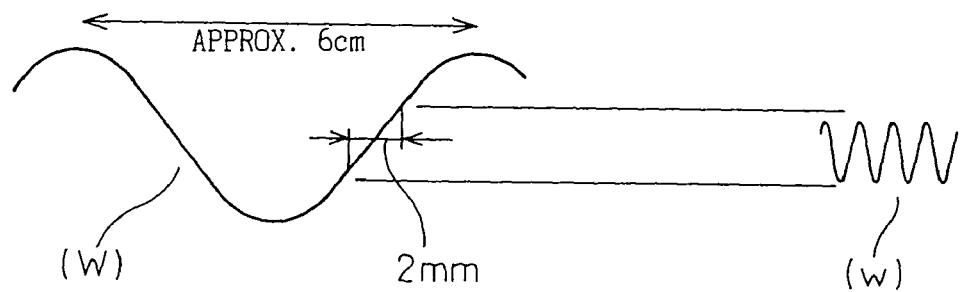
FIG. 8 is a diagram showing the waveform obtained when a breathing motion is detected by an object detection sensor which radiates a microwave of 2.45 GHz toward an object.

That is, FIG. 8 shows the waveform obtained when a breathing motion is detected by an object detection sensor which radiates a microwave of 2.45 GHz toward an object in the configuration shown in FIG. 3. At 2.45 GHz, the wavelength is 12 cm but, as the reflected wave travels a round trip, the effective wavelength can be considered to be one half of that, that is, 6 cm.

In FIG. 8, the waveform (W) shows the radiated microwave, while the waveform (w) represents the waveform of the signal produced by a breathing motion of 2 mm in amplitude and 0.5 Hz in frequency. The output waveform (w) signal does not contain a component due to the Doppler frequency shift obtained by the equation (1), but the up/down motion exhibited by the object is directly output. In this way, by adding the differentiating circuit, the minuscule signal corresponding to the breathing motion can be extracted. However, the problem is that the sensor output greatly differs depending on where in the waveform of the microwave the breathing motion of 2-mm amplitude is detected.

Figure 9:
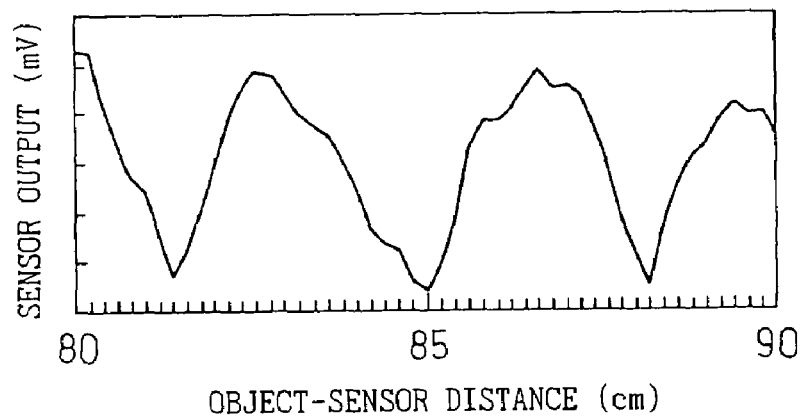
FIG. 9 is a diagram showing how sensor output changes depending on the distance between the sensor and the object.

FIG. 9 is a diagram showing how the sensor output changes depending on the distance between the sensor and the object exhibiting the up/down motion of 2-mm amplitude. As can be seen from the figure, a point where the output signal is hardly obtained appears at intervals of 3 cm. This shows that the output signal becomes small at points corresponding to the peaks and troughs of the electromagnetic field of the microwave generated by the sensor.

Figure 10:
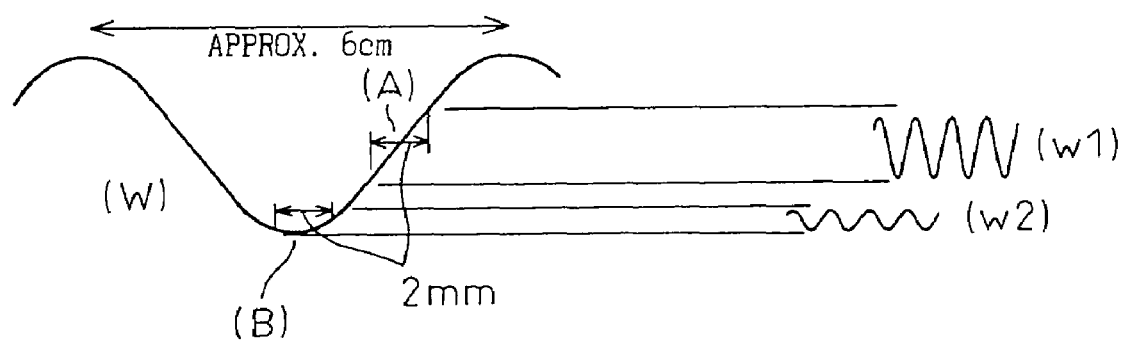
FIG. 10 is a diagram showing a waveform generated by the sensor when an up/down motion being exhibited by the object is detected at a position where the electromagnetic field of the microwave changes abruptly, for comparison with a waveform generated by the sensor when the motion is detected at a position where the electromagnetic field changes little.

FIG. 10 is a diagram showing the waveform of the electromagnetic field produced by the 2.45-GHz microwave radiated from the sensor, along with the waveform of the signal generated by the sensor when the up/down motion being exhibited by the object is detected at a position where the electromagnetic field changes abruptly and the waveform of the signal generated when the motion is detected at a position corresponding to a trough (or a peak) where the electromagnetic field changes little.

As shown in FIG. 10, the signal waveform (w1) generated by the minuscule up/down motion detected at the position (A) where the electromagnetic field of the microwave (W) changes abruptly exhibits a large amplitude; on the other hand, the amplitude of the signal waveform (w2) generated by the minuscule up/down motion detected at the position (B) where the electromagnetic field changes little is small, and this makes it difficult to detect the breathing motion.

In view of this, the present inventor thought that if the frequency of the microwave as the transmitted wave was increased, the amplitude of the signal waveform produced by the minuscule up/down motion would not decrease appreciably, regardless of where in the waveform of the microwave the up/down motion was detected.

Figure 11A:
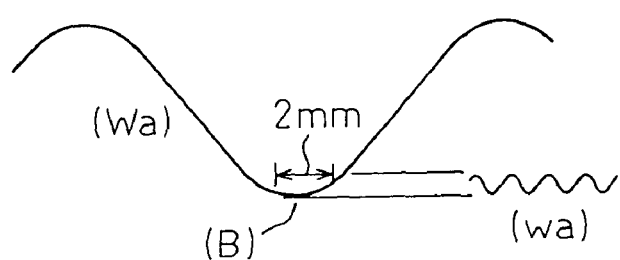
FIGS. 11A and 11B are diagram showing waveforms generated when a minuscule motion is detected, one when the frequency of the microwave is 2.45 GHz and the other when the frequency is higher.
Figure 11B:
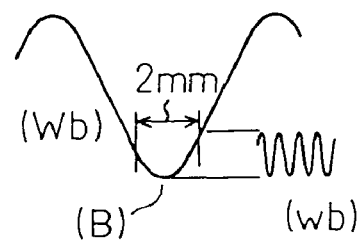

FIGS. 11A and 11B show waveforms generated when the minuscule motion is detected, one when the frequency of the microwave is 2.45 GHZ and the other when the frequency is higher, for example, 5 GHz. FIG. 11A shows the waveform (Wa) when the frequency of the microwave is 2.45 GHz; as can be seen, the amplitude of the signal waveform generated by the minuscule up/down motion detected at the position (B) where the electromagnetic field changes little is small, as shown by the waveform (wa). On the other hand, FIG. 11B shows the waveform (Wb) when the frequency of the microwave is 5 GHZ; as can be seen, the signal waveform generated by the minuscule up/down motion likewise detected at the position (B) where the electromagnetic field changes little exhibits a larger amplitude, as shown by the waveform (wb).

In theory, if the transmitting frequency of the microwave is not increased that much, the minuscule signal associated with the breathing motion can be detected. However, in reality, it then becomes difficult to discriminate the minuscule signal due to the presence of noise. In the case of a conventional electronic device, the minimum signal amplitude that can be discriminated from noise is about 10% of the full range amplitude. In FIG. 10, a maximum output is obtained at the position (A), and a minimum output at the position (B). When the signal obtained at the position (A) is assumed to be a full range signal, then the transmitting frequency with which the amplitude of the minimum signal obtained at the position (B) is 10% of the full range is 4.7 GHz when the amplitude of the object's up/down motion is 2 mm. The present invention thus solves the first problem by using the above method.

Figure 1:
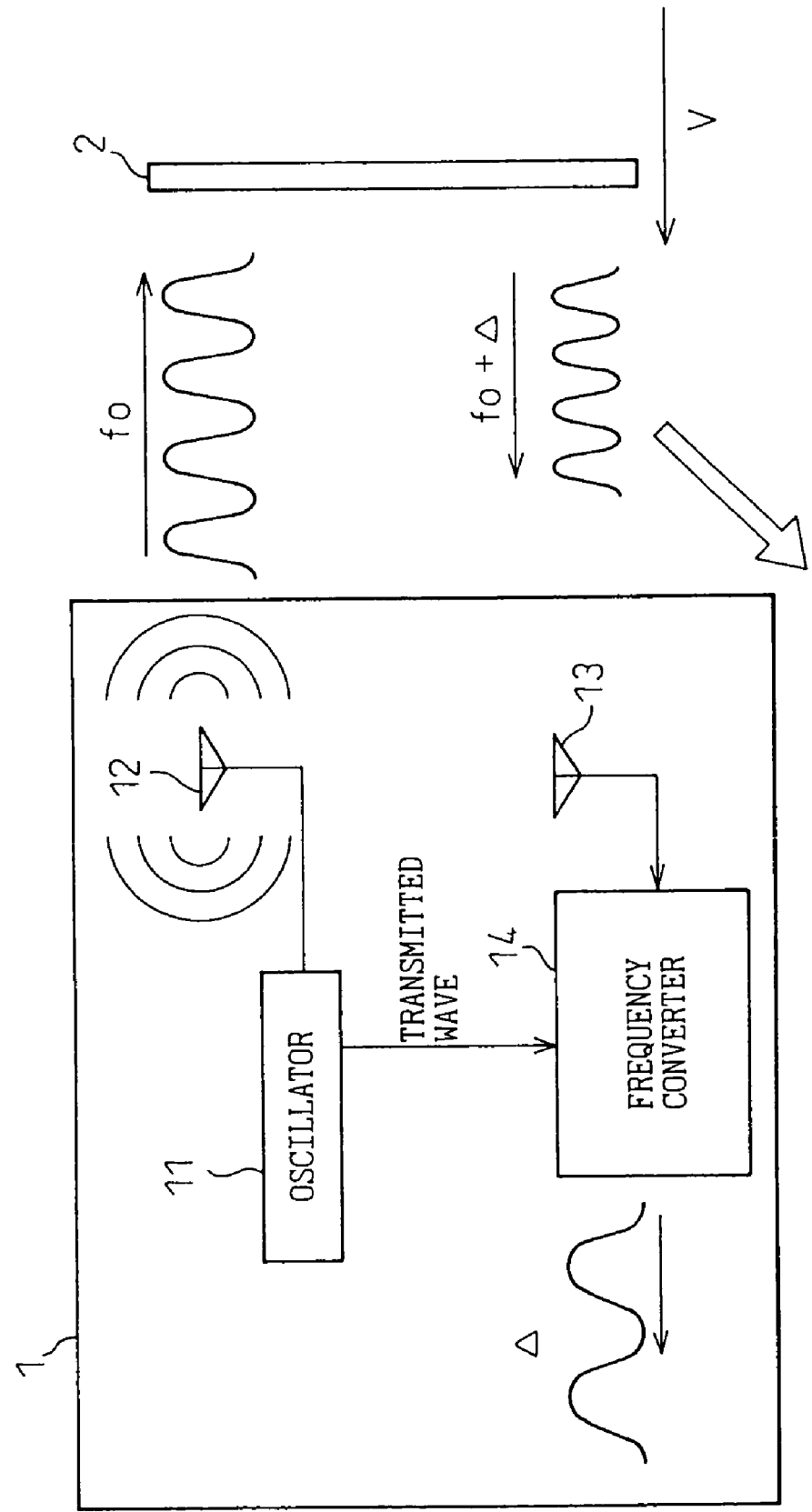
FIG. 1 is a diagram showing one example of a sensor for detecting the presence of a human.
Figure 2:
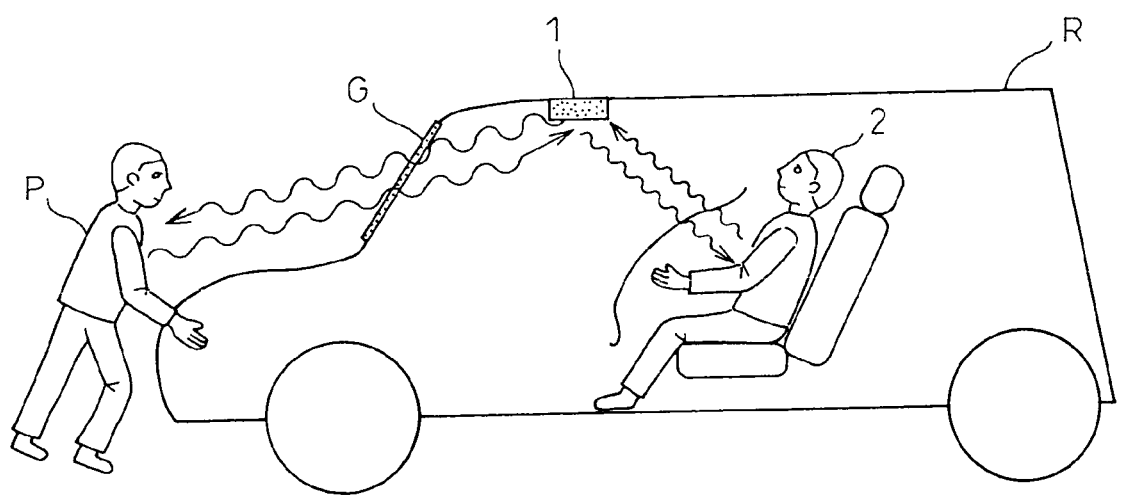
FIG. 2 is a diagram for explaining the possibility of a sensor detecting a movement outside a vehicle.

On the other hand, in order not to detect the movement of a person or a car outside the vehicle, as explained with reference to FIG. 2, there is a need to use a microwave of a frequency that does not pass through the vehicle's windshield.

Figure 12:
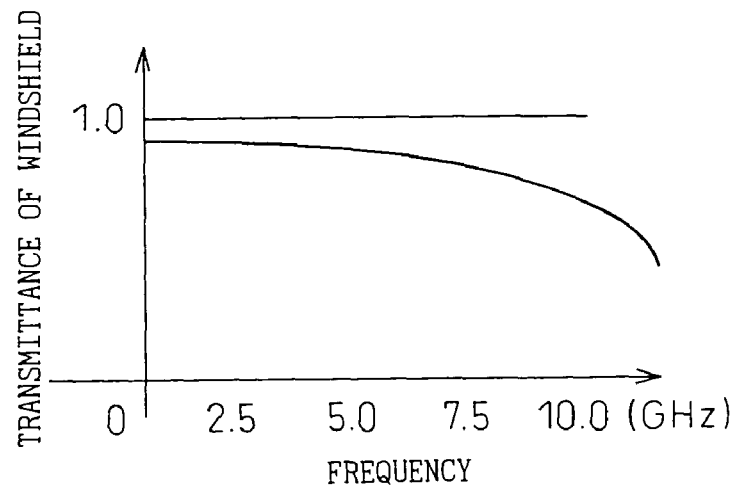
FIG. 12 is a diagram showing the relationship between the frequency of the microwave and the transmittance of a windshield.

FIG. 12 is a graph showing the relationship between the frequency of the microwave and the transmittance of the windshield. As shown by the graph, the transmittance of the windshield decreases greatly for frequencies around 4.7 GHz. Accordingly, when the microwave of 4.7 GHz or higher frequency is used, the chance of detecting the movement of a person or a car outside the vehicle decreases. The present invention thus solves the second problem by using the above method.

Next, the method of the present invention for detecting a human body in a vehicle will be described below with reference to several embodiments.

EMBODIMENT 1

When there is a human in the vehicle, the breathing motion of the human body causes a fluctuation in the reflected wave of the microwave emitted from the sensor. As earlier described, when a microwave of a higher frequency is used, the sensor becomes less sensitive to movements outside the vehicle, but there still exists the possibility that the sensor may detect a movement outside the vehicle if the amount of movement is large. However, a movement outside the vehicle, for example, the movement of a person passing by, is of a one-off nature. On the other hand, when there is a human in the vehicle, the breathing motion of the human body is detected continuously. Accordingly, when the reflected wave of the microwave fluctuates continually, for example, for a few minutes, it can be determined that there is a human inside the vehicle. Otherwise, it can be determined that the detected movement is a movement outside the vehicle.

Figure 13:
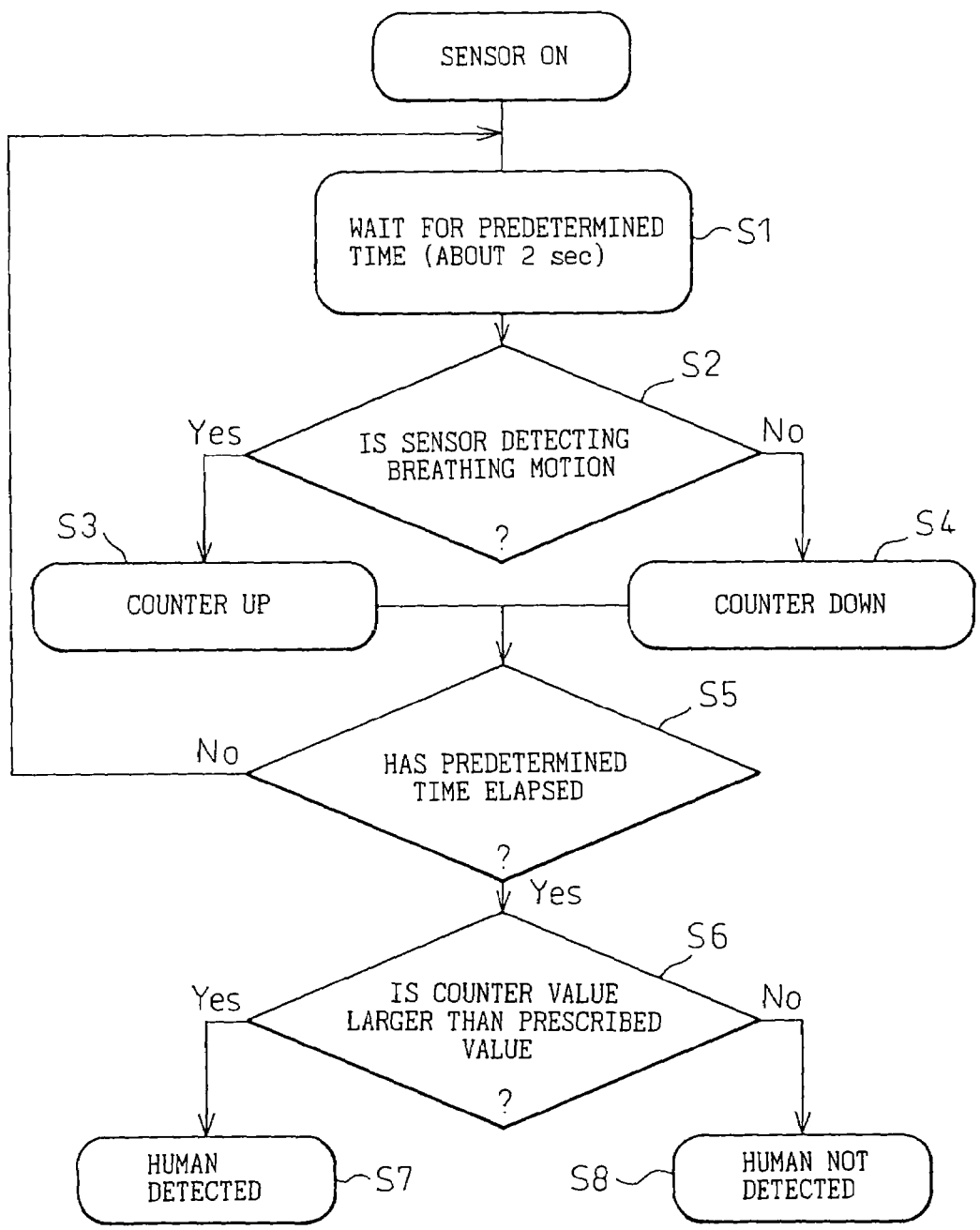
FIG. 13 is a flowchart illustrating one embodiment of the present invention.

FIG. 13 is a flowchart illustrating one embodiment of the method of the invention based on the above concept. In FIG. 13, when the sensor is turned on, the process waits for a predetermined time, for example, two seconds (S1), during which it is determined whether the sensor detects a breathing motion (S2). If Yes, the counter counts up while the breathing motion is being detected (S3), and it is determined whether a predetermined time, for example, three minutes, has elapsed (S5). If Yes, it is then determined whether the counter value is larger than a prescribed value (S6). If Yes, it is determined that a human is detected (S7). If the counter value is not larger than the prescribed value in S6 (No), it is determined that no human is detected (S8). If, in S5, the predetermined time has not yet elapsed (No), the process returns to S1.

On the other hand, if it is determined in S2 that the sensor is not detecting a breathing motion (No), the counter counts down (S4), and it is determined whether the predetermined time, for example, three minutes, has elapsed (S5). If Yes, it is then determined whether the counter value is larger than the prescribed value (S6). The process thereafter is the same as that described above.

Control operations in the above flowchart are performed by the microcomputer 6 in FIG. 3.

EMBODIMENT 2

When a person is left in a vehicle, the life of that person may be endangered if the temperature inside the vehicle rises excessively high or drops excessively low. It is therefore effective to activate the sensor when the temperature inside the vehicle has risen or is about to rise excessively high and to detect the presence or absence of a person inside the vehicle, rather than monitoring the presence or absence of a person at all times. By not detecting the presence or absence of a person at all times, the chance of detecting a movement outside the vehicle can be reduced.

Figure 14:
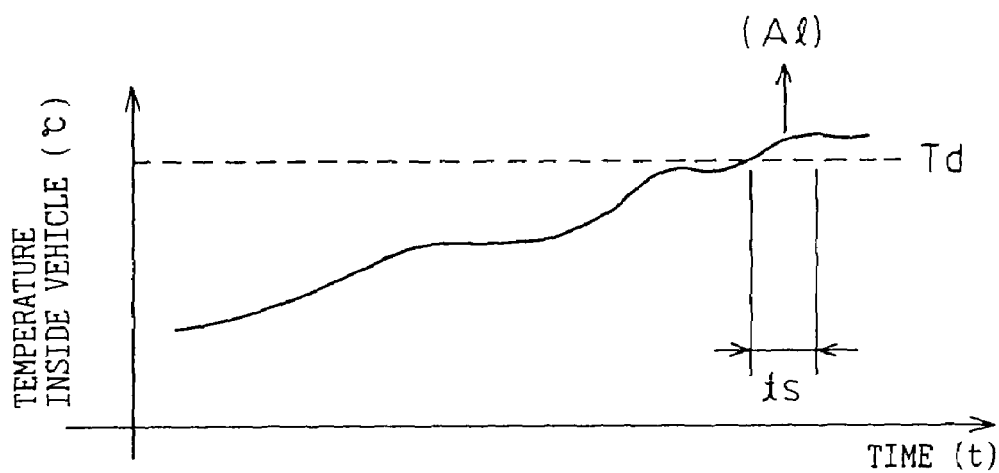
FIG. 14 is a diagram showing a method according to the present invention.

FIG. 14 is a diagram showing the method of the invention based on the above concept. In FIG. 14, the abscissa represents the time, and the ordinate the temperature inside the vehicle. The temperature inside the vehicle is monitored at all times, and the sensor is activated when the temperature inside the vehicle rises excessively high. As shown in FIG. 14, when the temperature inside the vehicle reaches a dangerous temperature Td indicate by a dashed line, or rises close to the dangerous temperature, the sensor is activated within a prescribed time (ts) and, if the presence of a human is detected inside the vehicle, an alarm (Ar) is generated. In this way, warning of potential danger can be issued by activating the sensor only when necessary.

The above description has dealt with the case where the temperature rises excessively high, but the warning can also be given in a similar manner when the temperature drops excessively low. The same applies to the embodiments hereinafter given.

EMBODIMENT 3

In the foregoing second embodiment, the sensor is activated after the temperature has reached a dangerous level, to detect the presence or absence of a human in the vehicle. In the second embodiment, however, there is a time lag of a few minutes between the time the sensor is activated and the time the presence or absence of a human in the vehicle is detected, and during that time, damage may be caused to the human left in the vehicle. To avoid such a situation, in the third embodiment, a device for monitoring the gradient of the temperature inside the vehicle is provided, and the sensor is activated in advance when it is predicted by the device that the temperature inside the vehicle is likely to rise (or fall) to a dangerous level.

Figure 15:
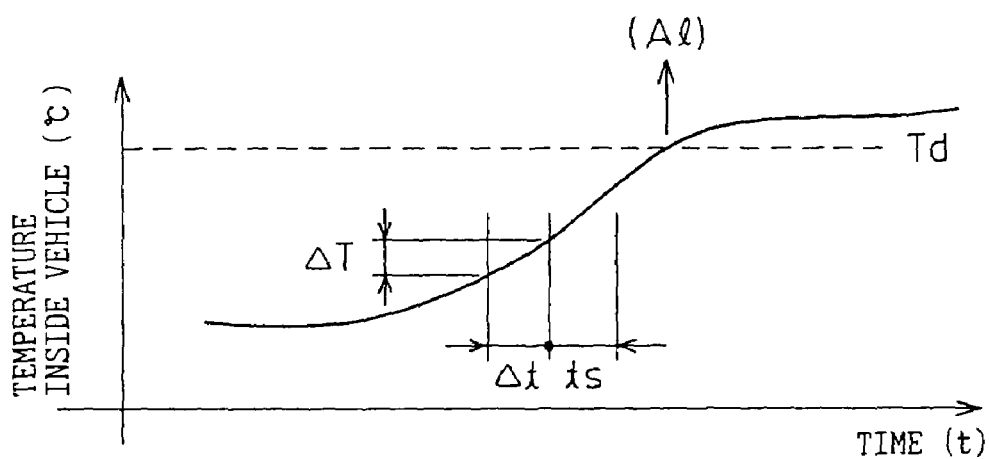
FIG. 15 is a diagram showing a method according to the present invention.

FIG. 15 is a diagram showing the method of the invention based on the above concept. In FIG. 15, the abscissa represents the time and the ordinate represents the temperature inside the vehicle. The temperature inside the vehicle is constantly monitored and, when the temperature gradient exceeds a predetermined value, the sensor is activated by predicting that the temperature inside the vehicle is likely to become excessively high. For example, as shown in FIG. 15, when the temperature inside the vehicle rises by $\Delta T$ during the time $\Delta t$, if $\Delta T/\Delta t$ is larger than the predetermined value, the sensor is activated for a specified time (ts) before the temperature reaches the dangerous level, by predicting that the temperature inside the vehicle is likely to become excessively high. When the presence of a human is detected inside the vehicle, and when the temperature reaches the dangerous temperature (Td) indicted by dashed line, an alarm (Ar) is generated. In this way, warning of potential danger can be issued by activating the sensor only when necessary.

EMBODIMENT 4

In the second and third embodiments, the time to activate the sensor was determined based on prescribed conditions. However, even when the rate of change of the temperature is mild and there is, therefore, no pressing need to detect the presence or absence of a human, the temperature might rise abruptly at any moment. Even so, keeping the sensor operating at all times is inefficient, and there is also the possibility that the sensor may issue a false alarm, for example, by detecting a person strolling around the vehicle. In view of this, according to the method of the invention, a device for monitoring the temperature gradient is provided and, when the rate of change of temperature inside the vehicle is mild, the sensor is operated for a predetermined length of time at random timing; if the presence of a human is detected inside the vehicle then, when the temperature inside the vehicle thereafter reaches a dangerous level, an alarm is generated.

Figure 16:
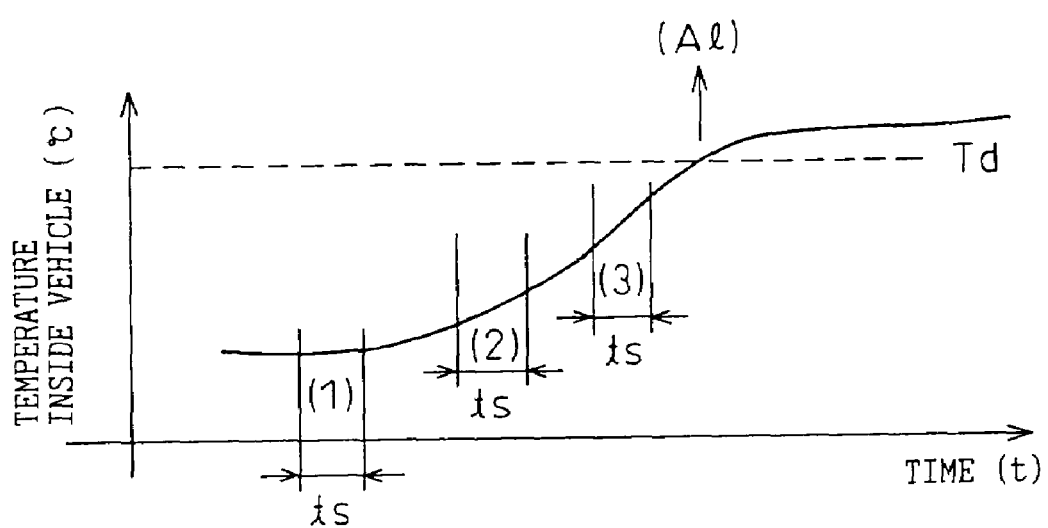
FIG. 16 is a diagram showing a method according to the present invention.

FIG. 16 is a diagram showing the method of the invention based on the above concept. In FIG. 16, the sensor is operated for a predetermined length of time at random timing, as shown by (1), (2), and (3). If the presence of a human is detected inside the vehicle, then when the temperature inside the vehicle thereafter reaches the dangerous level, the alarm is generated. For example, when the presence of a human is not detected at time (1) or (2) but is detected at time (3.) then, when the temperature thereafter reaches the dangerous temperature Td, the alarm (Ar) is generated. On the other hand, when the presence of a human is detected at time (2) but is not detected at time (3), the alarm is not issued even when the temperature thereafter reaches a dangerous temperature.

Figure 17:
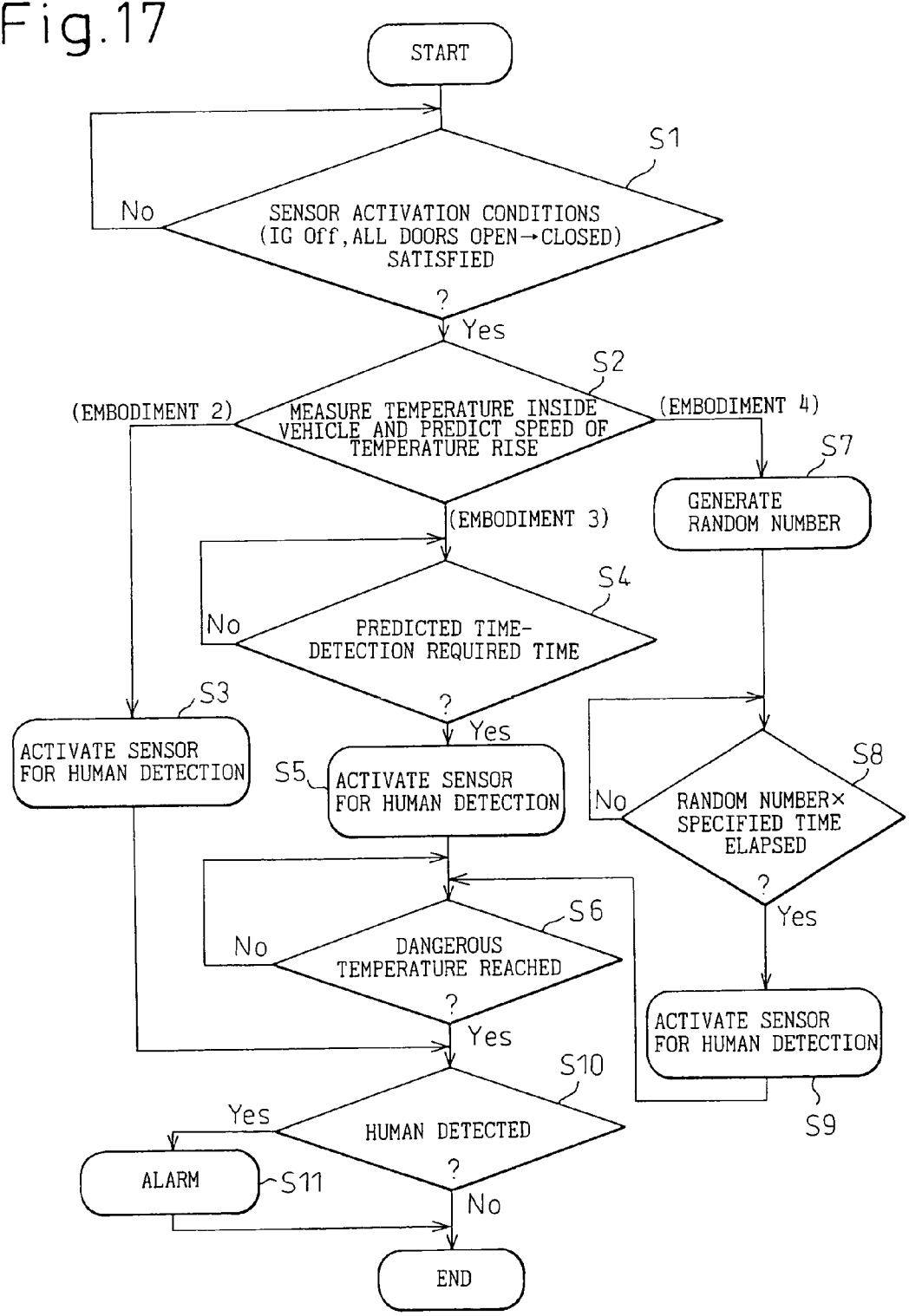
FIG. 17 is a diagram showing a flowchart for the embodiments of the present invention.

FIG. 17 is a diagram showing the flowchart for the above-described second, third, and fourth embodiments. First, it is determined whether sensor activation conditions are satisfied or not (S1). The activation conditions include, for example, ignition off, all doors closed, etc. Next, the speed of temperature rise inside the vehicle is predicted (S2).

If, as a result of the prediction, the temperature is likely to reach a dangerous temperature or if the temperature has already reached a dangerous temperature (Embodiment 2), then the sensor is activated to detect the presence or absence of a human inside the vehicle (S3). Then, it is determined whether the presence of a human has been detected or not (S10); if Yes, the alarm is issued (S11).

On the other hand, if it is determined, as a result of the prediction, that the temperature inside the vehicle is rising and is likely to reach a dangerous temperature, for example, within tens of minutes (Embodiment 3), the time that will elapse until the dangerous temperature is reached is predicted and summed with the time (5 or 10 minutes) required to detect the presence of a human, and it is determined whether or not the time to detect the presence of a human by the sensor is required before the dangerous temperature is reached; if Yes, the sensor is activated in advance to detect the presence or absence of a human (S5). Next, it is determined whether the dangerous temperature is reached or not (S6); if Yes, then it is determined whether the presence of a human has been detected or not (S10). If Yes, the alarm is issued (S11).

On the other hand, if it is predicted that the temperature is not very likely to reach a dangerous temperature, or that it will take a long time to reach a dangerous temperature (Embodiment 4), a random number is generated (S7). Then, it is determined whether a specified time based on the random number has elapsed or not (S8). If No, the same step is repeated, and if Yes, the sensor is activated to detect the presence or absence of a human (S9). Next, it is determined whether a dangerous temperature has been reached or not (S6); if Yes, then it is determined whether the presence of a human has been detected or not (S10). If Yes, the alarm is issued (S11).

EMBODIMENT 5

Normally, it is unlikely that a person would be left inside a vehicle for too a long time, for example, for 24 hours. Therefore, it would not be necessary to detect the presence or absence of a human after such a long time has elapsed. In such cases, the sensor is deactivated and the system is turned off to reduce the dark current of the vehicle.

Figure 18:
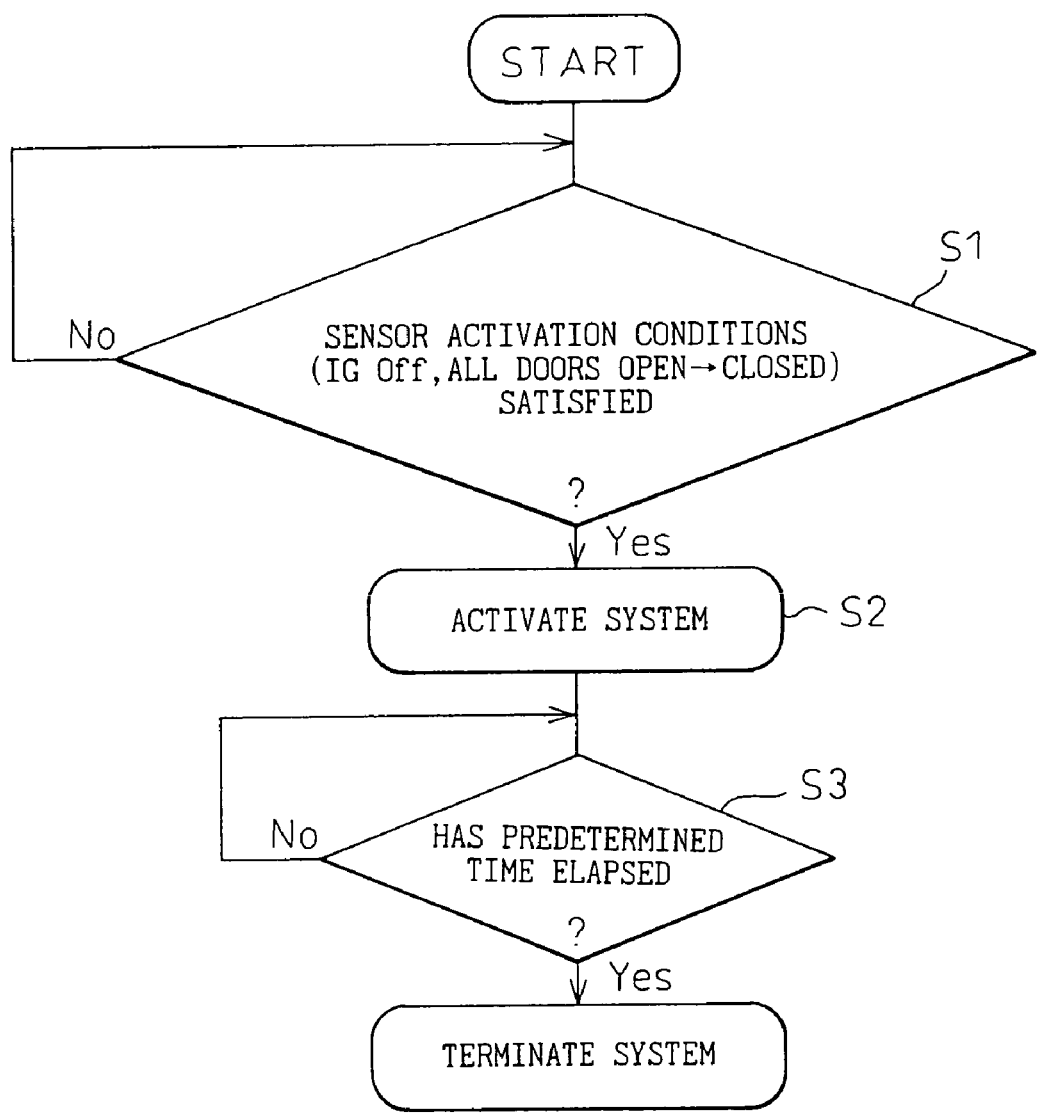
FIG. 18 is a diagram showing a flowchart for a further embodiment of the present invention.

FIG. 18 is a flowchart illustrating the method of the invention based on the above concept. First, it is determined whether sensor activation conditions are satisfied or not (S1). The activation conditions include, for example, ignition off, all doors closed, etc. If Yes, the system is activated (S2). If No, it is again determined whether the activation conditions are satisfied or not. After the system is activated, it is determined whether a predetermined time, for example, 24 hours, has elapsed or not (S3). If Yes, the system is terminated. If No, the process returns to S3.

EMBODIMENT 6

Each of the embodiments so far described has dealt with the method of how the presence of a human is detected by the sensor and when the alarm is to be issued.

The present embodiment checks whether the sensor is operating normally. For example, when the vehicle is moving at 5 km/h or at higher speed, it is determined that a person, including the driver, is undoubtedly present in the vehicle. In this case, if the sensor does not detect the presence of a human, it can be determined that the sensor is faulty.

FIG. 19 is a flowchart illustrating the method of the invention based on the above concept. First, it is determined whether a self-diagnostic condition is satisfied or not (S1). The self-diagnostic condition in this case is, for example, a vehicle speed of 5 km/h or higher. If Yes, the sensor is activated (S2). Next, it is determined whether the presence of a human is detected or not (S3). If Yes, it is determined that the sensor is operating normally (S4). On the other hand, if No, it is determined that the sensor is faulty (S5) because the presence of a human was not detected when a human is actually present.

The invention claimed is:

1. A method for detecting a human body in a vehicle, comprising:
    radiating a transmitted wave from a sensor provided in said vehicle;
    obtaining a synthetic wave based on said transmitted wave and a reflected wave from a breathing human body;
    detecting the presence or absence of a human in said vehicle on the basis of an envelope of said synthetic wave;
    obtaining a relative velocity of the breathing human body by differentiating the envelope of said synthetic wave; and
    detecting the presence or absence of a human in said vehicle on the basis of the relative velocity.

2. A method for detecting a human body in a vehicle as claimed in claim 1, wherein the frequency of said transmitted wave is 4.7 GHz or higher.

3. A method for detecting a human body in a vehicle as claimed in claim 1, wherein, when the presence of a human is detected continuously for a predetermined length of time, it is determined that a human is present in the vehicle.

4. A method for detecting a human body in a vehicle as claimed in claim 1,
    wherein when the interior of said vehicle reaches a temperature dangerous to a human, said sensor is activated.

5. A method for detecting a human body in a vehicle as claimed in claim 1, wherein, when the presence of a human has not been detected throughout the duration of a predetermined time, said sensor is deactivated.

6. A method for detecting a human body in a vehicle as claimed in claim 1, wherein said sensor is operated in a situation where a person is undoubtedly present in said vehicle, and if the presence of the person is detected, it is determined that said sensor is operating normally, but if the presence of the person is not detected, it is determined that said sensor is faulty.

7. A method for detecting a human body in a vehicle as claimed in claim 1, wherein the detecting comprises detecting the presence or absence of a human substantially only within said vehicle.

8. A method for detecting a human body in a vehicle, wherein a synthetic wave is obtained which represents the synthesis of a transmitted wave radiated from a sensor and a reflected wave returned from a breathing human body, and the presence or absence of a human in said vehicle is detected from the envelope of said synthetic wave, and wherein a device for monitoring a temperature gradient inside said vehicle is provided, and said sensor is activated in advance when it is predicted by said device that the interior of said vehicle is likely to reach a dangerous temperature.

9. A method for detecting a human body in a vehicle, wherein a synthetic wave is obtained which represents the synthesis of a transmitted wave radiated from a sensor and a reflected wave returned from a breathing human body, and the presence or absence of a human in said vehicle is detected from the envelope of said synthetic wave, and wherein a device for monitoring temperature gradient inside said vehicle is provided, and when the rate of change of temperature inside said vehicle is mild, said sensor is operated at a random timing for a predetermined length of time.

10. A method for detecting a human body in a vehicle as claimed in any one of claims 4 to 9, wherein, when the interior of said vehicle reaches a dangerous temperature, and when the presence of a human is detected, an alarm is issued.

11. A method for detecting a human body in a vehicle as claimed in claim 10, wherein said dangerous temperature is a temperature high enough or low enough to present a hazard to a human body.

* * * * *